(12) United States Patent
Pisharodi

(10) Patent No.: US 8,480,742 B2
(45) Date of Patent: Jul. 9, 2013

(54) TOTAL ARTIFICIAL DISC

(75) Inventor: Madhavan Pisharodi, Brownsville, TX (US)

(73) Assignee: Perumala Corporation, Brownsville, TX (US)

( * ) Notice: Subject to any disclaimer, the term of this patent is extended or adjusted under 35 U.S.C. 154(b) by 0 days.

(21) Appl. No.: 11/195,880

(22) Filed: Aug. 2, 2005

(65) Prior Publication Data

US 2007/0043441 A1    Feb. 22, 2007

(51) Int. Cl.
*A61F 2/44*    (2006.01)

(52) U.S. Cl.
USPC .................................. 623/17.13; 623/17.12

(58) Field of Classification Search
USPC ........................................ 623/17.11–17.16
See application file for complete search history.

(56) References Cited

U.S. PATENT DOCUMENTS

| | | | | |
|---|---|---|---|---|
| 5,865,846 A * | 2/1999 | Bryan et al. | .................. | 128/898 |
| 5,888,223 A * | 3/1999 | Bray, Jr. | ..................... | 623/17.16 |
| 6,102,950 A * | 8/2000 | Vaccaro | ..................... | 623/17.16 |
| 6,264,695 B1 * | 7/2001 | Stoy | ............................. | 623/17.16 |
| 6,402,785 B1 * | 6/2002 | Zdeblick et al. | ........... | 623/17.16 |
| 6,419,704 B1 * | 7/2002 | Ferree | ....................... | 623/17.12 |
| 6,533,817 B1 * | 3/2003 | Norton et al. | .............. | 623/17.16 |
| 7,282,065 B2 * | 10/2007 | Kirschman | ................ | 623/17.15 |
| 2004/0049279 A1 * | 3/2004 | Sevrain | ....................... | 623/17.13 |
| 2004/0220669 A1 * | 11/2004 | Studer | ........................ | 623/17.12 |

FOREIGN PATENT DOCUMENTS

DE    4213771 C1 *    9/1993

OTHER PUBLICATIONS

"Frame." Merriam-Webster Online Dictionary [online], [retrieved on Dec. 9, 2007]. Retrieved from the Internet <URL: http://www.m-w.com/>.*

"Bridge." Merriam-Webster Online Dictionary [online], [retrieved on Dec. 9, 2007]. Retrieved from the Internet <URL: http://www.m-w.com/>.*

"Arm." Merriam-Webster Online Dictionary [online], [retrieved on Dec. 9, 2007]. Retrieved from the Internet <URL: http://www.m-w.com/>.*

* cited by examiner

*Primary Examiner* — Pedro Philogene
*Assistant Examiner* — Lynnsy Schneider
(74) *Attorney, Agent, or Firm* — D'Ambrosio & Menon, PLLC

(57) ABSTRACT

An artificial disc prosthesis having load-bearing characteristics that mimic those of the normal, healthy intervertebral disc so as to provide resist flexion and axial compression of the spine in a way that preserves normal spinal function. The disc prosthesis includes three main components, a frame, a cushion molded over the frame, and a sac containing a hydrogel for maintaining disc height that is confined within a cavity in the cushion. Disc height is changed by increasing and/or decreasing the amount of hydrogel in the sac in accordance with the particular needs of the patient into which the artificial disc is implanted. Also provided is a frame for an artifical intervertebral disc that allows the axis of rotation of the spine to shift in a manner that replicates, or mimics, the normal function of the intervertebral disc.

22 Claims, 2 Drawing Sheets

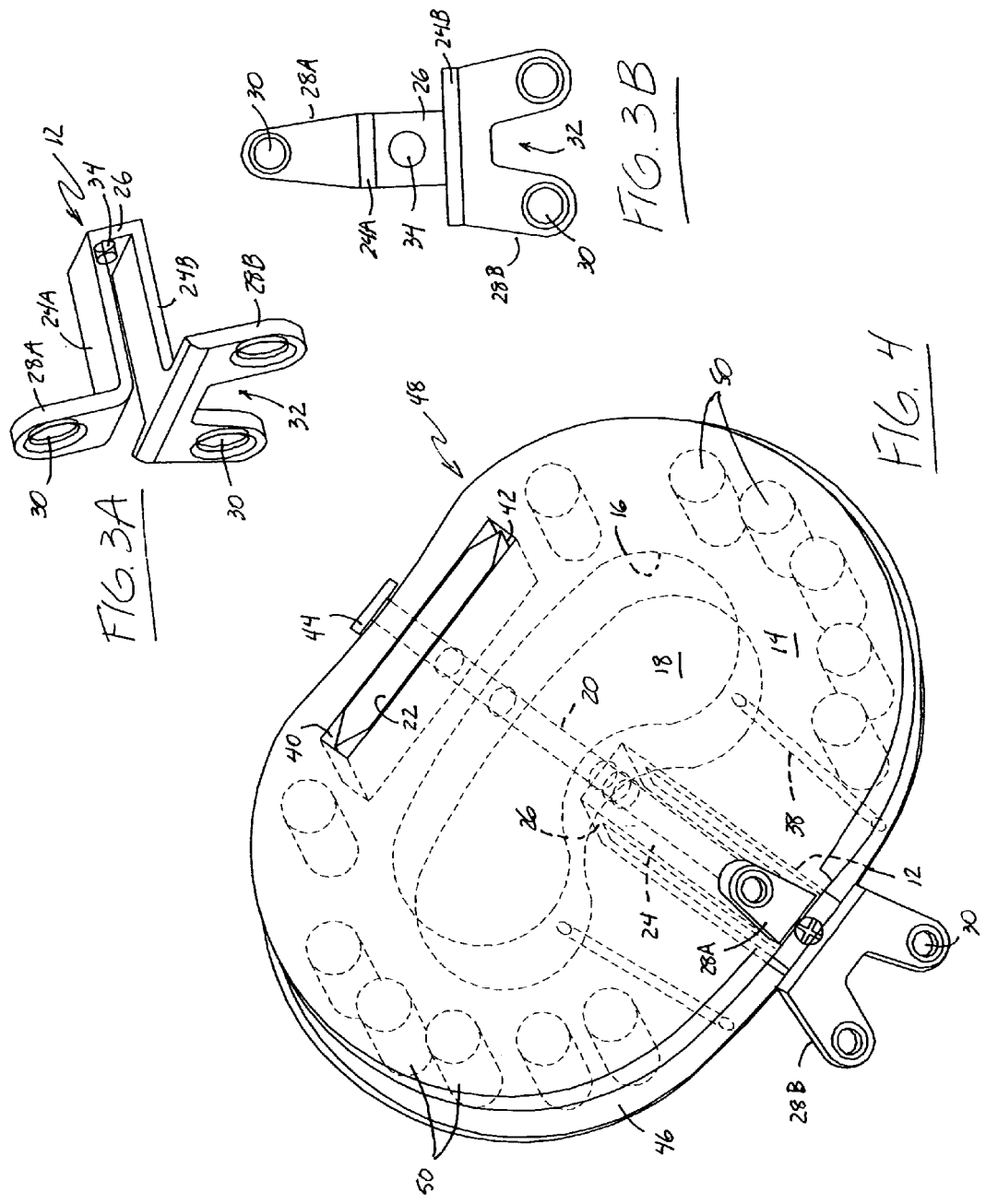

TOTAL ARTIFICIAL DISC

BACKGROUND OF THE INVENTION

The present invention relates to an artificial disc that does not include a joint or significant sliding portions, but which still maintains the flexibility of the spine, as well as the cushioning effect of the disc, after surgical replacement of an intervertebral disc. In more detail, the present invention relates to an artificial disc, intended for use in surgical replacement of an intervertebral disc, that retains the properties of cushioning and resistance to flexure of the spine, as well as allowing other normal range of motions, that characterize the healthy, normal intervertebral disc.

The injured, deformed, diseased, and/or degenerated human spine is a source of great pain in many patients, and there are many approaches to management, treatment, and/or prevention of that pain, including surgical intervention. One particularly vexing source of spinal pain and/or dysfunction is the damaged intervertebral disc. Healthy intervertebral discs are a necessity to pain-free, normal spinal function, yet disc function is all too frequently impaired by, for instance, disease or injury.

The anatomy of the intervertebral disc correlates with the biomechanical function of the disc. The three major components of the disc that are responsible for the function of the disc are the nucleus pulposus, annulus fibrosus, and cartilagenous endplate. The nucleus pulposus is the centrally located, gelatinous network of fibrous strands, surrounded by a mucoprotein gel, that prevents buckling of the annulus and maintains the height of the disc (and therefore, provides the cushioning effect and resistance to spinal flexure that are so important to spinal function) through osmotic pressure differentials. The water content of the disc changes in accordance with the load on the spine, water being driven out of the pulposus under heavy load. The annulus fibrosus encapsulates the disc, resisting both tension and compression loads and bearing axial loads. The vertebral endplates are cartilagenous in nature and "sandwich" the other components of the disc, distributing load over the entire disc and providing stability during normal spinal movements. The three elements work in cooperative fashion to facilitate disc function, and impairment of any of the elements compromises the functions of the other elements.

The two main surgical treatments of the intervertebral disc include total disc and nuclear replacement, but unfortunately, both treatments represent a number of compromises that simply do not provide normal disc function. The total artificial disc prosthesis is a total prosthetic replacement of the annulus fibrosus and nucleus pulposus with an endplate that interfaces with the patient's own vertebral endplates. Capturing and securing the total disc prosthesis to the host vertebral endplates can be a challenge because of the asymmetrical and cyclic loads placed upon the spine that can place excessive stresses on both the host bone and the interface between the prosthesis and the endplates, resulting in early loss of fixation. Many presently available total disc prostheses are designed to mimic the function of normal joints, but in that aspect, they are non-physiological in the sense that the normal spine does not have actual joints or sliding functions, but does have an inherent shock absorbing function. This lack of cushioning and shock absorbing function may be the contributing factor for the settling of the prosthesis into the vertebral body. For a summary of some of the disadvantages and limitations of known disc replacements, reference may be made to C. M. Bono and S. R. Garfin, History and Evolution of Disc Replacement, The Spine Journal, Vol. 4, pp. 145S-150S (2004) and E. G. Santos, et al., Disc Arthroplasty: Lessons Learned from Total Joint Arthroplasty, The Spine Journal, Vol. 4, pp. 182S-189S (2004).

Nuclear replacement is intended to replace a damaged nucleus pulposus with a device that is intended to restore disc height while maintaining the kinematics of the gel that comprises the healthy, intact nucleus pulposus. Although less invasive of the spine, implant extrusion and migration of the implant are all too frequent complications of nuclear replacement surgery. Some of the disadvantages and limitations of known devices for disc replacement are summarized in C. M. Bono and S. R. Garfin, History and Evolution of Disc Replacement, The Spine Journal, Vol. 4, pp. 145S-150S (2004) and in A. N. Sieber and J. P. Kostuik, Concepts in Nuclear Replacement, The Spine Journal, Vol. 4, pp. 322S-324S (2004).

It is, therefore, an object of the present invention to provide a total artificial intervertebral disc that is intended to overcome the disadvantages and limitations of these prior art devices comprising a frame, a cushion molded over the frame, and a screw passing through said frame and at least a portion of said cushion. An anchor is mounted to the screw for selectively engaging the vertebrae adjacent the intervertebral disc space when the frame, having the cushion molded thereover, is inserted into the space between two adjacent vertebrae and the screw is turned, thereby resisting anterior-posterior movement of the artificial disc relative to the adjacent vertebrae.

Another object of the present invention is to provide a total artificial disc that maintains the normal range of motion of the spine and provides a cushioning function that approximates the normal function of the intervertebral disc under compression load.

Another object of the present invention is to provide a total artificial disc that is comprised of three main components that together function to provide the cushioning provided by cooperation of the three components of the normal intervertebral disc.

Another object of the present invention is to provide a total artificial disc in which the axis of rotation translates in the anterior-posterior direction in a manner that approximates normal disc function.

Another object of the present invention is to provide a total artificial disc that is adapted for use in adjacent segments of the spine.

Another object of the present invention is to provide a frame for an intervertebral disc prosthesis comprised of two spaced apart, substantially parallel arms, a bridge connecting the arms at one end, a "U"-shaped ear extending at approximately a right angle from the end of one of the arms opposite the bridge and having a hole formed therein for receiving a screw, and a "Y"-shaped ear extending at approximately a right angle from the end of one of the arms opposite the bridge having holes formed in both forks of the Y-shaped ear for receiving screws, the frame being comprised of a material that tends to return to its original shape after the frame is subjected to either a compression or tension load.

Other objects, and the many advantages of the present invention, will be made clear to those skilled in the art in the following detailed description of several preferred embodiments of the present invention and the drawings appended hereto. Those skilled in the art will recognize, however, that the embodiments of the invention described herein are only examples provided for the purpose of describing the making and using of the present invention and that they are not the only embodiments of artificial discs that are constructed in accordance with the teachings of the present invention.

SUMMARY OF THE INVENTION

The present invention addresses the above-described problem by providing an artificial intervertebral disc comprising a frame having a cushion molded over the frame. A screw passes through the frame and at least a portion of the cushion. An anchor is mounted to the screw for selectively engaging the adjacent vertebrae when the frame, having the cushion molded thereover, is inserted into the space between two adjacent vertebrae and the screw is turned.

In another aspect, the present invention provides a frame for an intervertebral disc prosthesis comprised of spaced apart, substantially parallel arms, a bridge connecting the arms at one end, a "U"-shaped ear extending at approximately a right angle from the end of one of the arms opposite the bridge and having a hole formed therein for receiving a screw, and a "Y"-shaped ear extending at approximately a right angle from the end of one of the arms opposite the bridge and having holes formed in both forks of the Y-shaped ear for receiving screws, the frame being comprised of a material that tends to return to its original shape after the frame is subjected to either a compression or tension load.

BRIEF DESCRIPTION OF THE DRAWINGS

Referring now to the figures.

FIGS. 3A and 3B are perspective and front elevational views of the frame of the artificial disc of FIG. 1 before the cushion is molded over the frame.

FIG. 4 is a top plan view of an alternative embodiment of an artificial disc constructed in accordance with the teachings of the present invention.

DETAILED DESCRIPTION OF THE PREFERRED EMBODIMENT(S)

Figure 1:
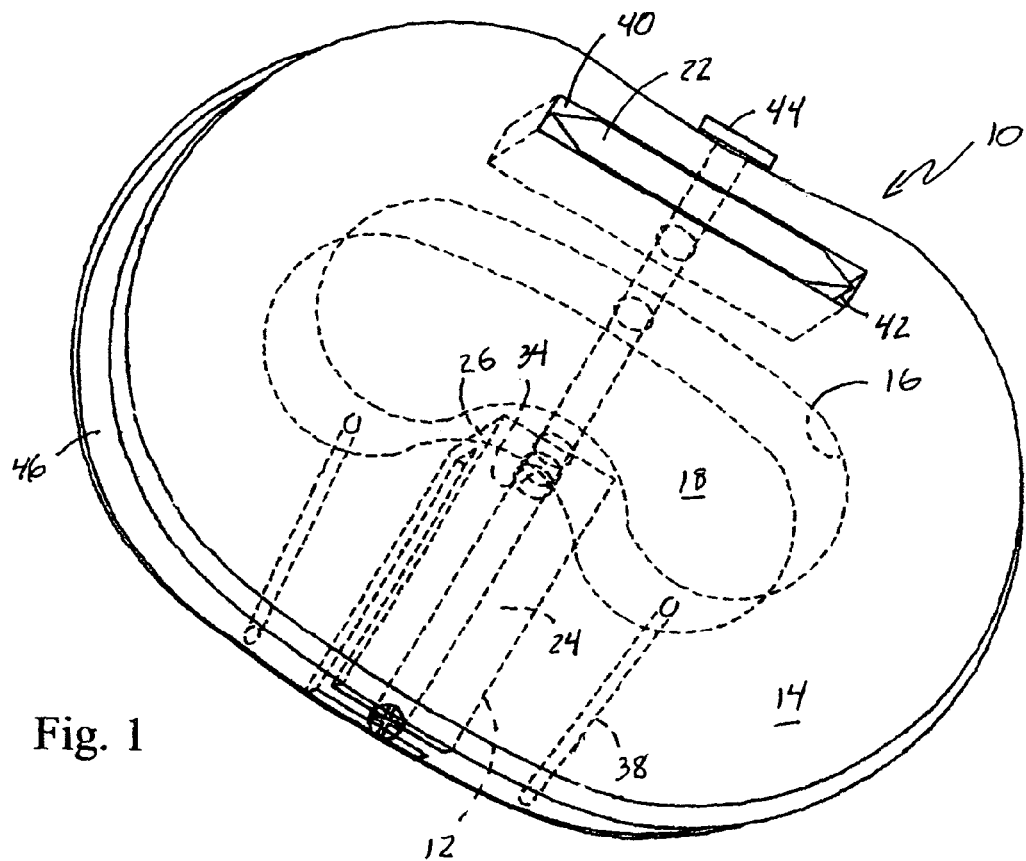
FIG. 1 shows a perspective view of one embodiment of an artificial intervertebral disc constructed in accordance with the teachings of the present invention.
Figure 2:
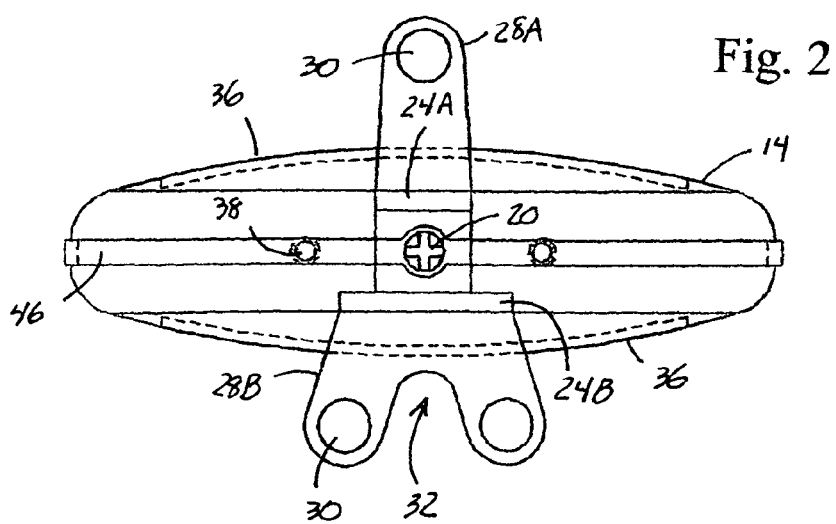
FIG. 2 is a side elevational view of the artificial disc of FIG. 1.

Referring now to the figures, FIGS. 1 and 2 indicate a first embodiment of an artificial disc constructed in accordance with the teachings of the present invention generally at reference numeral 10. Artificial disc 10 is comprised of three main components, each described in more detail below, a frame 12, cushion 14 molded over 30 frame 12, and sac 16 contained within a cavity 18 formed in cushion 14. A fourth component, comprised of screw 20 and anchor 22 is also shown in FIG. 1. Although shown in the figures in a configuration that reflects the use of the artificial disc 10 for replacement of an intervertebral disc in the lumbar region of the spine, those skilled in the art will recognize from the following description that, with appropriate changes in size and configuration, the artificial disc of the present invention can also be utilized to advantage for total disc replacement in the cervical spine.

Frame 12 is better illustrated in FIGS. 3A-3B, and by reference to those figures, it can be seen that frame 12 is comprised of two spaced apart arms 24 connected at one end by a bridge 26. One or both of the ends 25 of the arms 24 opposite bridge 26 are provided with ears 28 having holes 30 formed therein for receiving a screw (not shown in FIG. 3) for securing frame 12 to the bodies of the vertebrae (not shown) adjacent the intervertebral disc space into which artificial disc 10 is inserted. In the preferred embodiment shown, both ends of arms 24 are provided with ears 28, the ear 28A on the end of one arm 24A being shaped in the form of an inverted "U," and the ear 28B on the end of the other arm 24B being shaped in the form of an inverted "Y" and having two holes 30 formed therein, the portion of ear 28B between the holes 30 being cutout at 32 to form the "fork" of the "Y"-shaped ear 28B. This arrangement of "U"-and "Y"-shaped ears 28A and 28B allows the use of the artificial disc 10 of the present invention in the intervertebral disc spaces of successive segments of the spinal column. When secured to the body of the adjacent vertebra, the "U"-shaped ear 28A of one artificial disc extends into the cutout portion 32 of the "Y"-shaped ear 28B secured to the body of that same vertebra. As best shown in FIG. 3B, the bridge 26 of frame 12 is provided with a hole 34 for a purpose to be made clear below.

In the preferred embodiment, frame 12 is comprised of a material that tends to return to its original shape after the frame is subjected to either a compression or tension load. In other words, when the disc 10 is inserted into the intervertebral disc space, it is subjected to both compression and tension loads as the spine flexes and as the patient moves during his/her normal daily routine, and when subjected to compression and tension loads, the frame deforms. Under compression, the ends 25 of the arms 24 opposite bridge 26 tend to move closer to each other and when in tension, the ends 25 of the arms 24 opposite bridge 26 tend to move further apart; in other words, the arms 24 of frame 12 deviate from their original spaced apart position (in the preferred embodiment shown, the two arms are substantially parallel, but those skilled in the art who have the benefit of this disclosure will recognize that the invention is not limited to a frame having parallel arms) when under compression or tension force. When the respective compression or tension force is relieved, the frame 12 tends to return to its original shape, i.e., the ends 25 of arms 24 opposite bridge 26 return to their original spaced relationship, and the arms assume their original, spaced apart relationship. When subjected to loads in this manner, frame 12 acts as both a "backbone" and as a spring to help both bear compression loads and relieve tension loads in a manner that mimics normal disc function. Note also that, when the artificial disc 10 of the present invention is inserted into the intervertebral disc space, the bridge 26 of frame 12 is positioned posteriorally relative to the ends of arms 24 opposite bridge 26. The spring function of frame 12 is advantageous because, as the patient bends forward, the ends of arms 24 opposite bridge 26 are subjected to compression loads, and the further the patient bends, the more the material comprising frame 12 tends to resist the compression load, providing the spring function discussed above. Further, biomechanical studies of normal, healthy spines have shown that the axis of rotation (the weight-bearing center of the intervertebral disc) translates anteriorally and posteriorally as the spine flexes, and the variable resistance provided by this configuration and placement of frame 12 in the intervertebral disc space helps provide this normal front-to-back shift in the axis of rotation, so that the total artificial disc of the present invention replicates that shifting in the axis of rotation. Materials that are characterized by this spring-like function when formed into the frame 12 include, but are not limited to stainless steel, titanium and titanium alloys, cobalt-chrome (Co—Cr) alloys, cobalt-chromium-molybdenum (Co—Cr—Mo), and medical grade (inert) polymeric plastics such as polyethylene, all as known in the art.

As noted above, the cushion 14 is molded over frame 12 (best shown in FIG. 2), and from that description of the structural relationship of frame 12 and cushion 14, it can be surmised that cushion 12 is preferably molded from a resilient, polymeric material. Although not limited to these materials, in the preferred embodiment, cushion 14 is molded from a biocompatible, viscoelastic polymer such as silicone, a urethane such as a polycarbonate urethane, or a polyurethane. As best shown in FIG. 1, the cushion 14 is molded in a shape that approximates the shape of the normal intervertebral disc; by reference to FIG. 2, it can be seen that the top and bottom surfaces 36 of cushion 14 are arched so that cushion 14 is thicker in the center than at its periphery. This shape of cushion 14 is referred to as being biconvex, e.g., both the top and bottom of cushion 14 are convex in both the anterior-posterior and side-to-side directions.

In the preferred embodiment shown, the top and bottom surfaces 36 of cushion 14 are provided with a textured or grooved surface (indicated generally by reference numeral 37) to facilitate the ingrowth of bone onto the surfaces 36. In a particularly preferred embodiment, the surfaces 36 of cushion 14 are covered with a porous or roughened titanium coating and perhaps even a layer of calcium phosphate for this purpose; other suitable coatings/surfaces are known in the art and include titanium wire mesh, plasma-sprayed titanium, porous cobalt-chromium and bioactive materials such as hydroxyapatite and the aforementioned calcium phosphate.

As noted above, the central portion of cushion 14 is provided with a cavity 18 having a sac 16 contained therein. Although the cavity 18 shown in the figures is kidney-shaped so as to approximate the shape of the nucleus pulposus of a normal intervertebral disc, those skilled in the art who have the benefit of this disclosure will recognize that the cavity need not be shaped in this shape and that, depending upon the particular pathology that causes the disc replacement, it may even be advantageous to shape the cavity 18 differently in contemplation of varying kinematic characteristics. The sac 16 is at least partially filled with a hydrogel such as a polyvinyl alcohol (PVA), synthetic silk-elastin copolymers, polymethyl- or polyethylmethacrylate, polyethylene or polyacrylonitrile that absorbs water and increases in volume upon absorption of water, thereby functioning to maintain disc height in a manner similar to the manner in which the healthy disc maintains proper spacing between adjacent vertebrae. To facilitate the absorption of water, the sac 16 is comprised of a material that is permeable to water and the cushion 14 of artificial disc 10 may be provided with a plurality of holes or channels (not shown) for allowing water to pass through the material comprising cushion 14 and access the permeable sac 16 containing the hydrogel. Materials that may be used to advantage as the sac 16 include woven polyethylene, woven and non-woven biocompatible synthetic fibers and other materials as known in the art. Because the sac 16 is contained within cavity 18, the strength of the material comprising sac 16 is not as important as the ability of that material to contain the hydrogel and pass water into and out of the hydrogel in a manner that mimics the absorption of water by the healthy nucleus pulposus.

As best shown in FIG. 2, the disc 10 of the present invention is provided with ports 38 through which hydrogel can be added or removed from the sac 16 in the cavity 18 of cushion 14. These ports 38 are comprised of channels that extend from the sac 16 to the periphery of cushion 14, and are preferably located on the periphery of cushion 14 adjacent the ears 28 of frame 12 since the disc 10 is implanted ventrally and the ears 28 therefore face the surgeon when the disc 10 is implanted in the intervertebral disc space, allowing access to ports 38 so that the surgeon can inject the hydrogel (or use a syringe to remove hydrogel) as needed to confer the desired amount of initial disc height to the implanted artificial disc. Once the desired disc height is obtained, the ports 38 are capped or plugged to prevent extrusion of the hydrogel contained within sac 16.

As is also apparent in FIGS. 1 and 2, the screw 20 extends from the periphery of cushion 14 through cushion 14 in an anterior-posterior direction. Anchor 22 is mounted to the shaft of screw 20 at a location that allows anchor 22 to reside in a cavity 40 formed in cushion 14 until the surgeon rotates the screw 20 to extend anchor 22 out of cavity 40 into contact with the cortical end plates of the adjacent vertebrae. The ends of anchor 22 are formed as points 42 to help anchor 22 dig into the bone of the adjacent vertebrae, helping anchor disc 10 in the intervertebral disc space and resisting extrusion or shifting of the disc 10 relative to the adjacent vertebrae. To provide additional rigidity to this anchoring arrangement, the screw passes through and is journaled in the above-described hole 34 in the bridge 26 of frame 12 and the screw 20 is capped by a rivet 44 (see FIG. 1) or similar structure on the periphery of cushion 14 opposite ears 28. Those skilled in the art who have the benefit of this disclosure will recognize that the cavity 40 in which anchor 22 resides before rotation of screw 20 need not be separate from the cavity 18 containing sac 16. However, for protection of the material comprising the sac 16 from physical damage as a result of the rotation of screw 20 and/or extension of anchor 22, it is preferred that the two cavities be separated by the material comprising cushion 14.

Referring also to FIGS. 1 and 2, it can be seen that the material comprising cushion 14 is provided with a band 46 that completely encircles the periphery of cushion 14. In addition to the physical strength conferred upon the cushion 14 by this band, acting to confine the material comprising cushion 14 to resist extreme compression loads, the band 46 cooperates with the hole 34 in the bridge 26 of frame 12 to provide an additional bearing point for the screw 20 and rivet 44.

Referring now to FIG. 4, a perspective view of an alternative embodiment of the artificial disc of the present invention is shown at reference numeral 48. Disc 48 is similar to disc 10 except that it is provided with a plurality of shock absorbing cells 50 distributed throughout the material comprising cushion 14. In one embodiment, the shock absorbing cells 50 are comprised of a spring confined within a sac that is likewise confined within the cavity of the material comprising cushion 14 so as to restrict the motion of the spring confined therein to upward and downward, and not side-to-side, motion. This arrangement of the shock absorbing cells helps provide variable resistance to the compression force exerted by side-to-side flexion of the spinal column. Those skilled in the art will recognize from this disclosure that the distribution of the shock absorbing cells 50 in cushion 14 may be changed in accordance with the particular pathology addressed by implantation of the artificial disc of the present invention. It may, for instance, be advantageous to locate more cells 50 on one side of the portion of the cushion 14 than the other if the patient's spinal column is deformed (congenitally or as a result of degeneration or injury) so as to provide extra resistance to compression loads on one side of the spinal column.

Those skilled in the art will recognize from this description that the disc 48 is characterized by three different levels, or sources, of resistance to compression loads, thereby providing the cushioning function that is lacking in the total disc prostheses that are currently available. The first contribution to the resistance to compression loads is provided by the material comprising the cushion 14, the second contribution is from the hydrogel contained within sac 16, and the third contribution is provided by the shock absorbing cells 50. The contribution provided by each of these components is capable of being adjusted by use of different volumes of hydrogel, different sizes and shapes of the cushion 14, and the number, type, and location of shock absorbing cells 50 to optimize the function of the artificial disc of the present invention for each particular patient.

In yet another alternative embodiment (not shown), the amount of resistance to compression force provided by shock absorbing cells 50 is adjustable in response to either the amount of compression on said cushion or in response to an external input. The adjustability is provided in a number of ways. In one embodiment, the resistance to compression load is adjusted by use of an electrical motor incorporated into each of the cells 50. The motor responds to an external input that can be provided in the form of a pulsed magnetic, radio, or other signal received by an antenna also located in the cells 50 that causes extension of a ram by the motor to extend the spring in the cell to provide additional resistance to compression loads. Alternatively, an electrical signal is generated by a piezo-electric wire embedded in or supported by the band 46 encircling the periphery of the cushion 14 or the band 46 is itself comprised of a piezo-electric material. Upon compression of the material comprising cushion 14, the periphery of cushion 14 has a tendency to increase in diameter, and that increase generates an electrical signal in the piezo-electric wire that increases the resistance to compression load provided by the cells in the same manner as in response to an external input. In a second embodiment, rather than a motor, the shock absorbing cells 50 are each provided with a spring confined within the cell that is comprised of a material that reacts to changes in magnetic, electrical, or thermal fields to increase or decrease the compression/tension characteristics of the spring. A similar effect can be achieved by the use of biomaterials that respond to changes in magnetic, electrical, or even thermal fields. Depending upon the particular biomaterial, it is not even necessary to confine the material within a sac forming the cell 50; instead, the cell 50 may consist of a hole or blind pocket in the material comprising cushion 14 that is filled with the material that responds to changes in magnetic, electrical, or thermal fields to increase or decrease the resistance to compression load.

Those skilled in the art who have the benefit of this disclosure will recognize that certain changes can be made to the component parts of the apparatus of the present invention without changing the manner in which those parts function and/or interact to achieve their intended result. By way of example, those skilled in the art who have the benefit of this disclosure will recognize that the amount of resistance to compression and/or tension load provided by the frame 12 depends on such factors as the length of the arms 24 and the material comprising the frame 12 and that although it may be appropriate to implant an artificial disc constructed in accordance with the teachings of the present invention having a frame with a certain level of resistance to compression/tension load, it may be that an intervertebral disc including a frame with a different level of resistance to compression/tension load is better suited for implantation in another patient. It will also be apparent to those skilled in the art that the same result can be obtained by inserting a block (not shown) having a hole therethrough into the frame 12 against bridge 26 before inserting screw 20 therethrough to effectively shorten the length of each of the arms 24 comprising frame 12. It will also be recognized by those skilled in the art that to obtain desirable load resistance properties, it may be advantageous to make the cushion 14 of a combination of materials, with an embedded layer of material having a second set of resilience and/or load-bearing characteristics, or as a laminated "sandwich" of polyurethane and other material(s), each material adding a unique component to the load bearing characteristics of the cushion 14. All such changes, and others that will be clear to those skilled in the art from this description of the preferred embodiments of the invention, are intended to fall within the scope of the following, non-limiting claims.

What is claimed is:

1. An artificial intervertebral disc comprising:
a frame;
a cushion molded over the frame;
a screw passing through the frame and at least a portion of the cushion;
an anchor mounted to the screw for selectively engaging the adjacent vertebrae when the frame, having the cushion molded thereover, is inserted into the space between two adjacent vertebrae and the screw is turned; and
a band extending around the periphery of the cushion, the screw passing through a hole in the band.

2. The artificial intervertebral disc of claim 1 wherein the cushion is provided with a central cavity having a sac therein, the sac containing a hydrogel.

3. The artificial intervertebral disc of claim 2 wherein the sac is comprised of a material that is permeable to water.

4. The artificial intervertebral disc of claim 2 additionally comprising an opening through the cushion for changing the amount of hydrogel within the sac.

5. The artificial intervertebral disc of claim 2 wherein the hydrogel added in the sac is changed to change the load-bearing characteristics of the cushion.

6. The artificial intervertebral disc of claim 1 wherein the frame comprises first and second spaced apart arms connected at one end by a bridge.

7. The artificial intervertebral disc of claim 6 wherein the frame is comprised of a resilient material so that the ends of the arms opposite the bridge move toward and apart from each other in response to changes in load.

8. The artificial intervertebral disc of claim 6 wherein an end of one or both of the arms of the frame opposite the bridge is provided with an ear having a hole therethrough for receiving a screw for securing the frame to an adjacent vertebra.

9. The artificial intervertebral disc of claim 8 wherein the end of one arm of the frame is provided with the ear having a hole therethrough for receiving a screw for securing the frame to an adjacent vertebra and the end of the other arm of the frame is provided with the ear having two spaced apart holes therethrough for receiving screws for securing the frame to a second adjacent vertebra, a portion of the ear between the holes being cut out.

10. The artificial intervertebral disc of claim 6 wherein the screw having the anchor mounted thereto passes through a hole in the bridge of the frame.

11. The artificial intervertebral disc of claim 1 additionally comprising a plurality of shock absorbing cells situated in the cushion.

12. The artificial intervertebral disc of claim 11 wherein the shock absorbing cells are adjustable in response to either the amount of compression on the cushion or in response to external input.

13. The artificial intervertebral disc of claim 1 wherein the anchor resides in a cavity formed in the cushion until the screw is rotated to cause the anchor to project out of the cavity to engage the adjacent vertebrae.

14. The artificial intervertebral disc of claim 1 wherein the cushion is comprised of polyurethane.

15. The artificial intervertebral disc of claim 1 wherein the frame is comprised of a material that tends to return to its original shape after the frame is subjected to either compression or tension.

16. An artificial intervertebral disc comprising:

a frame;

a cushion molded over the frame;

a screw passing through the frame and at least a portion of the cushion; and an anchor mounted to the screw for selectively engaging the adjacent vertebrae when the frame, having the cushion molded thereover, is inserted into the space between two adjacent vertebrae and the screw is turned, wherein the anchor resides in a cavity formed in the cushion until the screw is rotated to cause the anchor to project out of the cavity to engage the adjacent vertebrae.

17. The artificial intervertebral disc of claim 16 wherein the frame comprises a material selected from the one of the group consisting of surgical stainless steel, titanium, and a medical grade polymer.

18. The artificial intervertebral disc of claim 16 wherein the frame comprises first and second spaced apart arms connected at one end by a bridge.

19. The artificial intervertebral disc of claim 16 additionally comprising a band extending around the periphery of the cushion.

20. The artificial intervertebral disc of claim 16 wherein the screw passes through a hole in the band.

21. The artificial intervertebral disc of claim 16 wherein the frame is comprised of a material that tends to return to its original shape after the frame is subjected to either compression or tension.

22. The artificial intervertebral disc of claim 16 additionally comprising a plurality of shock absorbing cells situated in the cushion.

* * * * *